United States Patent [19]
Gaudette

[11] Patent Number: 5,367,265
[45] Date of Patent: Nov. 22, 1994

[54] MOISTURE-SENSING CONTROLLER FOR A CLOTHES DRYER

[75] Inventor: Marvin F. Gaudette, Rockton, Ill.

[73] Assignee: Eaton Corporation, Cleveland, Ohio

[21] Appl. No.: 45,155

[22] Filed: Apr. 12, 1993

[51] Int. Cl.$^5$ ............................................. G08B 13/18
[52] U.S. Cl. ............................................ 328/1; 328/3; 327/509; 327/74; 327/77
[58] Field of Search ............... 328/1, 3; 307/308, 310, 307/360, 362

[56] References Cited
U.S. PATENT DOCUMENTS 4,419,627 12/1983 Schmelzer ............................ 328/4
4,449,188 5/1984 Unoguchi et al. ..................... 328/4

Primary Examiner—Margaret Rose Wambach
Attorney, Agent, or Firm—Roger A. Johnston

[57] ABSTRACT

A moisture-sensing circuit for a clothes dryer separates the moisture-sensing and timing functions in a way that minimizes undesirable interaction and reduces effects of tolerances in components, temperature, and supply-voltage. Separate comparators are provided for (1) the resistance of the moisture sensor as compared with a first threshold and (2) the time since occurrence of the most recent moisture signal that exceeded the first threshold, as compared with a second threshold representing a predetermined delay.

5 Claims, 1 Drawing Sheet

MOISTURE-SENSING CONTROLLER FOR A CLOTHES DRYER

FIELD OF THE INVENTION

The invention relates to controllers for sensing the wetness of clothes in clothes-drying machines.

BACKGROUND

In some types of driers, clothes are tumbled in a rotating basket, and they brush against a moisture sensor in the machine. Their dryness is monitored by an electronic resistance-measuring circuit that involves peak moisture sensing and timing or averaging. With moisture-sensing controllers of the prior art, the moisture-sensing function often interacts undesirably with the timing or averaging function. Moreover, the tolerances of circuit components, temperature and voltage sometimes cause troublesome variations in the performance of the controllers.

SUMMARY OF THE INVENTION

In the instant invention, resistance of the clothes is compared for wetness with a first reference threshold. When wet clothes touch the sensor, if the wetness threshold is exceeded the circuit responds by switching ON a first comparator, which discharges a capacitor. When the wet clothes leave the sensor the resistance of the sensor increases above the first threshold, the first comparator switches OFF, and the capacitor starts to recharge gradually through a resistor. Repeated touching of the sensor by wet clothes repeatedly discharges the capacitor, preventing the voltage of the capacitor from rising to a second threshold level, which requires some time.

When the clothes become dry enough not to switch the first comparator ON, and therefore not to discharge the capacitor, the capacitor can gradually recharge enough to reach the second threshold. The time delay involved is a first timing function of the apparatus. The second comparator is then switched ON and its output turns ON a transistor switch. Thereupon, a bridge circuit becomes conductive and applies voltage to an AC timer, which performs a second timing function of the apparatus. The AC timer introduces an additional time delay during which the dryer continues to operated in order to make the clothes somewhat dryer than the threshold level detectable by the moisture sensor.

Accordingly, one object of the invention is to provide a circuit for sensing the wetness of clothes in a dryer, in which the moisture sensing function and first timing function are separated in such a way as to minimize their interaction and to minimize the effects of tolerances in components, temperature and supply voltage.

Another object is to provide a moisture-sensing circuit for a clothes dryer, in which the moisture-sensing threshold is readily adjustable without affecting the first timing function.

Another object is to provide a moisture-sensing circuit in which the first timing function is readily adjustable without affecting the moisture-sensing threshold.

Other objects will be apparent from the drawings, description and claims.

DESCRIPTION OF PREFERRED EMBODIMENT

Figure 1:
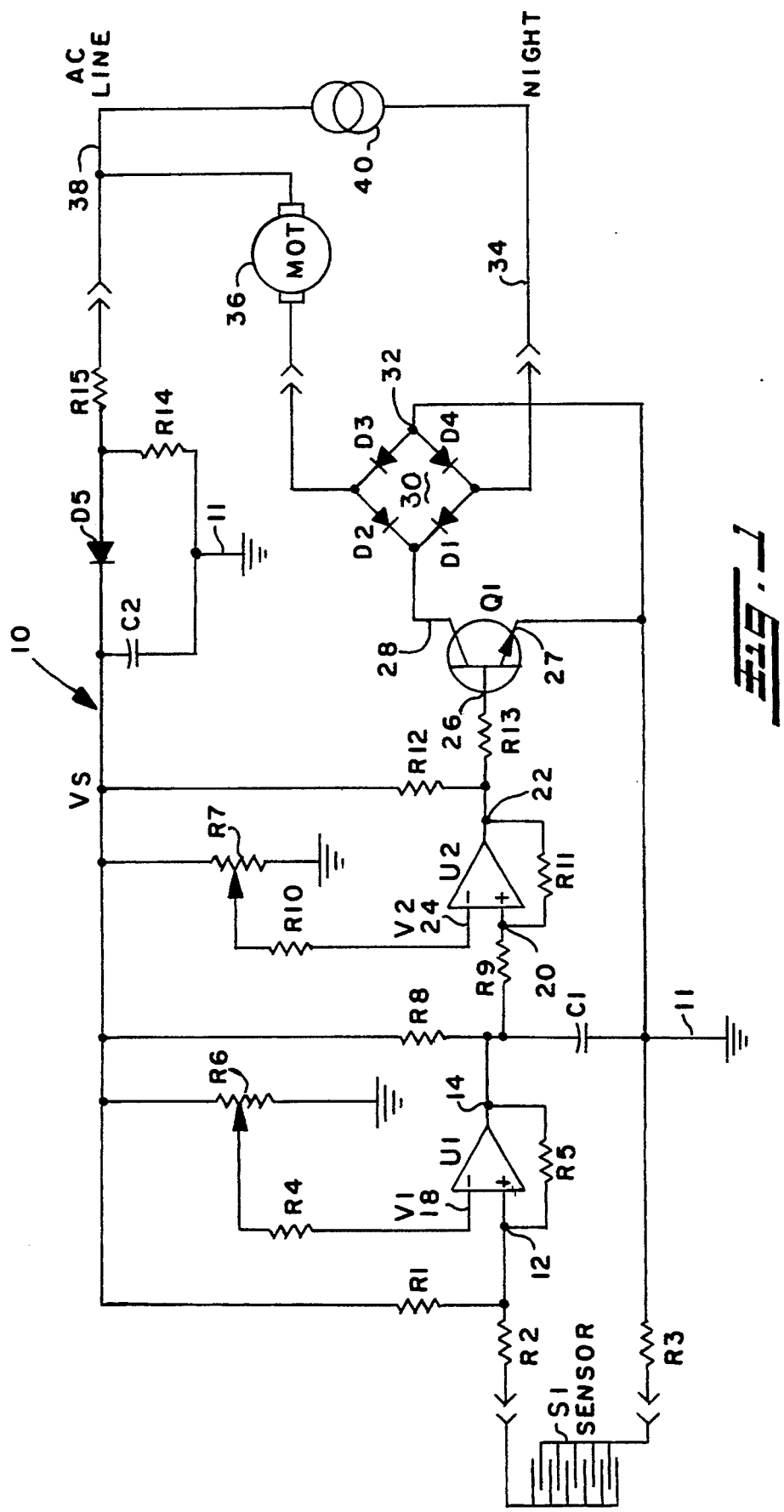
FIG. 1, the sole figure, is a schematic circuit diagram of the invented circuit.

Circuit Connections For Sensor S1 and First Comparator U1

In FIG. 1 a moisture-sensing controller for a clothes dryer is designated by reference number 10; it is a portion of a larger device that controls the dryer as a whole. The controller includes a moisture sensor S1 having two multiple-fingered electrodes that are interdigitated to increase the sensitivity to tumbling clothes that are being dried.

The sensor S1 is connected in series with two resistors R2 and R3. Resistor R3 connects to ground 11 of the control circuit. Resistor R2 connects to a non-inverting input terminal 12 of an operational amplifier U1. (Each of the operational amplifiers of FIG. 1 has also a power input terminal and a ground terminal, which are not shown.) The resistor Re also connects to a resistor R1, whose other end goes to a positive power supply bus labelled Vs.

The amplifier terminal 12 is also connected to a positive feedback resistor R5, whose other end is at output terminal 14 of the amplifier U1. Resistors R1, R2, R3 and the sensor S1 form a resistive voltage divider, from which an output signal is picked off for connection to the amplifier terminal 12.

Another resistive voltage divider is variable resistor R6, which is connected from the power supply bus Vs to ground 11. The transfer arm of R6 supplies a reference to an inverting input terminal 18 of the amplifier U1, where the voltage is designated V1. U1 is therefore arranged to be a voltage comparator, functioning as a static binary switch; and outputting a signal depending upon which of its input terminals has a higher voltage. U1 is referred to below as a first comparator. R6 can be adjusted to control the moisture threshold of the first comparator U1.

Turning now to the output circuit of the first comparator U1, terminal 14 is connected to a shunt capacitor C1 whose other plate is held at ground potential 11. A resistor R8 is connected from terminal 14 to the positive bus Vs. R8 provides a current path by which the capacitor C1 can be gradually charged, providing a first time delay, whenever terminal 14 is not shorting-circuiting the capacitor C1 to ground.

Circuit Connections For Second Comparator U2 and Switch Q1

The junction of resistor R8 and capacitor C1 is connected through a resistor R9 to a non-inverting input terminal 20 of a second operational amplifier US. At terminal 20 another resistor R11 is connected, its other end being at output terminal 22 of amplifier U2 to provide positive feedback.

A second input terminal 24 of amplifier U2 is an inverting input, whose voltage is designated V2. It is connected through a resistor R10 to the transfer arm of a variable resistor R7. If desired, the reference voltage level V2 at terminal 24 can be adjusted by means of R7. Thus the amplifier U2 compares the voltage at C1 with the reference voltage V2, which serves here as a capacitor-charge-level reference. U2 is referred to below as a second comparator.

A pull-up resistor R12 is connected from the amplifier output terminal 22 to the positive supply Vs. Another resistor, R13, detects the voltage at terminal 22 and, if the voltage is high enough, conducts a current to the base electrode 26 of an NPN transistor Q1. The emitter 27 of transistor Q1 is connected to ground 11, and the collector 28 is connected to a diode bridge 30. Transistor Q1 serves as a switch for turning the AC timer motor 36 ON and OFF.

Circuit Connections For Bridge 30 and Timer Motor 36

The bridge 30 comprises diodes D1, D2, D3 and D4. The collector 28 of Q1 is connected between diodes D1 and D2. The opposite corner 32 of the bridge 30, between D3 and D4, is at ground potential 11. The junction of diodes D1 and D4 is connected to a neutral line 34 of an AC power source 40. The remaining corner of bridge 30, at diodes D2 and D3, is connected to one terminal of the AC timer motor 36, whose other terminal is connected to an AC power line 38 of the source 40. The bridge circuit 30 and the transistor switch Q1 that controls it function as a DC controller for the AC timer motor 36.

The positive bus Vs receives power from the AC line 38 through a conventional rectifier subcircuit consisting of voltage-dropping resistors R15 and R14, a half-wave rectifier D5, and a shunt filter capacitor C2 connected to ground 11.

Operation When Wet Clothes Touch the Sensor

When the basket of the clothes dryer contains wet clothes and is rotating, the clothes frequently touch the exposed electrodes of the sensor S1. The conductive wet clothes enable current flow through the sensor, which reduces the voltage at terminal 12 of the first comparator U1. If the clothes are conductive enough that the voltage at terminal 12 decreases below the threshold voltage V1 (which is standing at terminal 18), comparator U1 switches its output at terminal 14 to a logic zero, which it does by effectively connecting terminal 14 internally to ground.

Capacitor C1 discharges to ground through the output of U1, and remains discharged so long as the voltage at terminal 12 remains below the first threshold reference voltage V1. The voltage at terminal 20 of U2 is lower than the threshold voltage V2 at terminal 24, and comparator U2 holds its output voltage (terminal 22) at a logic zero level. Transistor Q1 is therefore non-conductive, preventing current through the bridge 30. The timer motor 36 has no power.

Whenever the sensor becomes non-conductive, U1 produces a logic 1 at its output 14, and the capacitor starts to charge gradually due to current flow through the resistor R8. This creates a time delay between the cessation of current in the sensor S1 and the actuation of U2. Whenever the sensor is again touched by wet clothes the capacitor is again very rapidly discharged. When the sensor again becomes dry the capacitor must start charging again from zero voltage, so as to start its time delay anew, without turning on the timer motor. Thus the motor 36 remains without power so long as wet clothes touch the sensor S1 with sufficient frequency.

Operation When Sensor Indicates That Clothes Are Dry

After the clothes are relatively dry, there is negligible current through R1, R2, S1 and R3, so the voltage at input terminal 12 of comparator U1 is approximately equal to the supply voltage Vs. Because the voltage at terminal 12 then exceeds the reference voltage V1 at terminal 18, the output 14 of U1 is approximately equal to Vs, which will be referred to as a logic 1 output level. Resistor R5 holds the comparator forcefully at a logic 1 output level.

Even though the clothes occasionally touch the sensor S1 they do not cause the voltage at terminal 12 to rise as high as the U1 (first) reference threshold V1, so the output 14 of comparator U1 does not go to zero. The capacitor C1 then has enough time since its most recent discharge to charge up gradually to the U2 (second) reference threshold V2.

Comparator U2 has a greater voltage on its terminal 20 than the reference voltage V2 of its terminal 24, so its output terminal 22 is at a logic 1 level. Transistor Q1 receives a significant base current, so conduction can occur from collector 28 to the emitter 27.

During voltage lobes of the AC source 40 in which line 38 is positive with respect to line 34, conventional current flows from line 38 through timer motor 36, diode D2, transistor Q1 and diode D4 to line 34. On the other half-cyles, diodes D1 and D3 conduct. Hence the timer motor 36 is energized with complete AC cycles when the transistor Q1 is conductive. The timer 36 adds a predetermined time interval to the running time of the main dryer motor (not shown), after which the entire dryer is turned off.

The use of separate comparators U1 and U2 for wetness comparison and capacitor-charge comparison reduces the effects of tolerances in components, temperature, and supply-voltage.

Although the invention has been described in terms of the preferred embodiment, it can be practiced in many other forms. The scope of the invention is defined by the claims.

What is claimed is:

1. A moisture-sensing control circuit for a clothes dryer in which clothes are dried by tumbling, comprising:

sensor means for sensing the electrical resistance of said clothes when the clothes contact said sensor means, and for providing a wetness signal accordingly;

first comparator means, including means for providing a fixed predetermined wetness threshold, said first comparator means being for comparing (a) said wetness signal with (b) said fixed predetermined wetness threshold, and outputting a first output signal according to whether (a) or (b) is greater;

capacitor means connected to receive said first output signal, and including a capacitor connected for discharging when said first output signal indicates clothes wetness greater than said wetness threshold, and for charging gradually when said first output signal indicates wetness less than said wetness threshold;

second comparator means, including means for providing a capacitor-charge threshold, said second comparator means being for comparing (c) the charge of said capacitor means with (d) said capacitor-charge threshold, and outputting a second output signal according to whether (c) or (d) is greater.

2. A circuit as in claim 1 and wherein said first comparator means comprises means for adjustment of the level at which said wetness signal equals said wetness threshold.

3. A circuit as in claim 1 and wherein said means for providing a capacitor-charge threshold comprises means for adjustment of the level at which the charge of said capacitor means equals said capacitor-charge threshold.

4. A circuit as in claim 1 and wherein said means for providing a wetness threshold comprises means for providing an adjustable wetness threshold.

5. A circuit as in claim 1 and wherein said means for providing a capacitor-charge threshold comprises means for providing an adjustable capacitor-charge threshold.

* * * * *